(12) United States Patent
Smith et al.

(10) Patent No.: US 7,835,834 B2
(45) Date of Patent: Nov. 16, 2010

(54) METHOD OF MITIGATING DRIVER DISTRACTION

(75) Inventors: Matthew R. Smith, Westfield, IN (US); Gerald Witt, Carmel, IN (US); Harry Zhang, Chander, AZ (US)

(73) Assignee: Delphi Technologies, Inc., Troy, MI (US)

( * ) Notice: Subject to any disclaimer, the term of this patent is extended or adjusted under 35 U.S.C. 154(b) by 1162 days.

(21) Appl. No.: 11/484,873

(22) Filed: Jul. 11, 2006

(65) Prior Publication Data

US 2006/0287779 A1 Dec. 21, 2006

Related U.S. Application Data

(63) Continuation-in-part of application No. 11/130,360, filed on May 16, 2005, now abandoned.

(51) Int. Cl.
 *G06F 7/00* (2006.01)
(52) U.S. Cl. .................. 701/36; 701/45; 340/425.5; 340/575; 340/576
(58) Field of Classification Search .......... 701/1, 701/36, 45; 340/425.5, 576, 575
 See application file for complete search history.

(56) References Cited

U.S. PATENT DOCUMENTS

| | | | | |
|---|---|---|---|---|
| 5,859,686 A | * | 1/1999 | Aboutalib et al. | 351/209 |
| 5,867,587 A | * | 2/1999 | Aboutalib et al. | 382/117 |
| 6,004,314 A | * | 12/1999 | Wei et al. | 606/12 |
| 6,130,617 A | * | 10/2000 | Yeo | 340/575 |
| 6,426,702 B1 | * | 7/2002 | Young et al. | 340/576 |
| 6,580,996 B1 | * | 6/2003 | Friedrich | 701/96 |
| 6,873,714 B2 | * | 3/2005 | Witt et al. | 382/118 |
| 6,926,429 B2 | * | 8/2005 | Barlow et al. | 362/464 |
| 6,927,674 B2 | * | 8/2005 | Harter et al. | 340/425.5 |
| 6,927,694 B1 | * | 8/2005 | Smith et al. | 340/576 |
| 6,989,754 B2 | * | 1/2006 | Kisacanin et al. | 340/576 |
| 7,202,792 B2 | * | 4/2007 | Zhang et al. | 340/576 |
| 7,423,540 B2 | * | 9/2008 | Kisacanin | 340/576 |
| 7,460,940 B2 | * | 12/2008 | Larsson et al. | 701/49 |
| 2003/0201895 A1 | * | 10/2003 | Harter et al. | 340/575 |
| 2004/0090334 A1 | * | 5/2004 | Zhang et al. | 340/575 |
| 2006/0259206 A1 | * | 11/2006 | Smith et al. | 701/1 |

FOREIGN PATENT DOCUMENTS

| EP | 1723901 | 11/2006 |
|---|---|---|
| WO | 2004/034905 | 4/2004 |

* cited by examiner

*Primary Examiner*—Thomas G Black
*Assistant Examiner*—Wae Louie
(74) *Attorney, Agent, or Firm*—Jimmy L. Funke

(57) ABSTRACT

A driver alert for mitigating driver distraction is issued based on a proportion of off-road gaze time and the duration of a current off-road gaze. The driver alert is ordinarily issued when the proportion of off-road gaze exceeds a threshold, but is not issued if the driver's gaze has been off-road for at least a reference time. In vehicles equipped with forward-looking object detection, the driver alert is also not issued if the closing speed of an in-path object exceeds a calibrated closing rate.

6 Claims, 8 Drawing Sheets

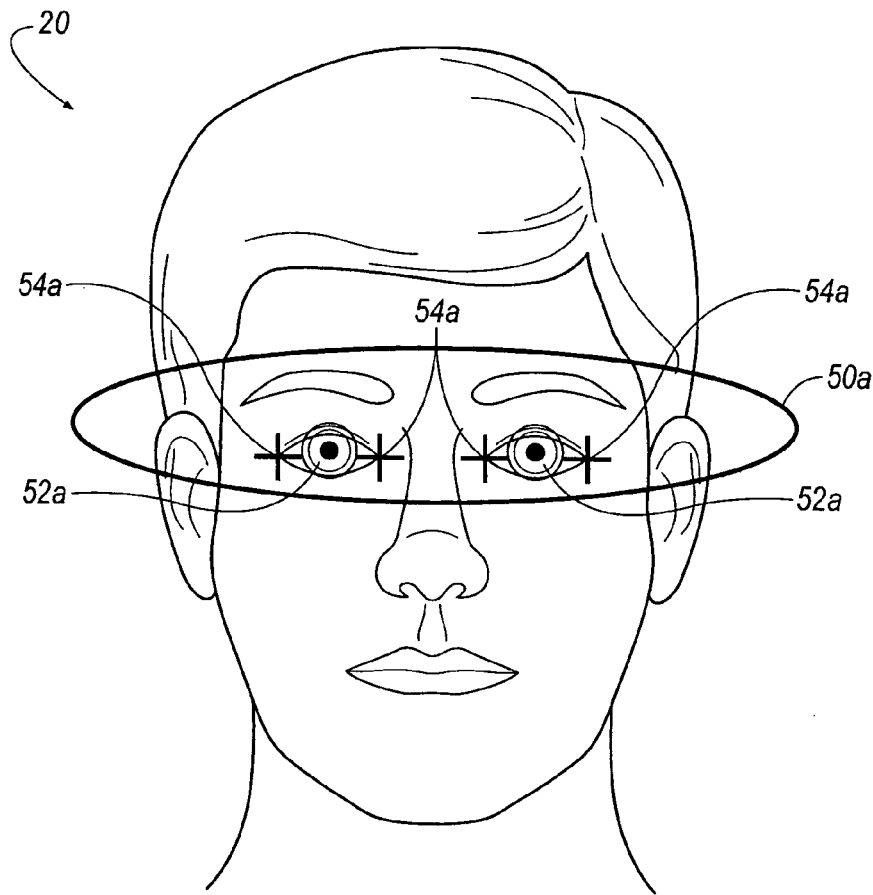
FIG. 5A
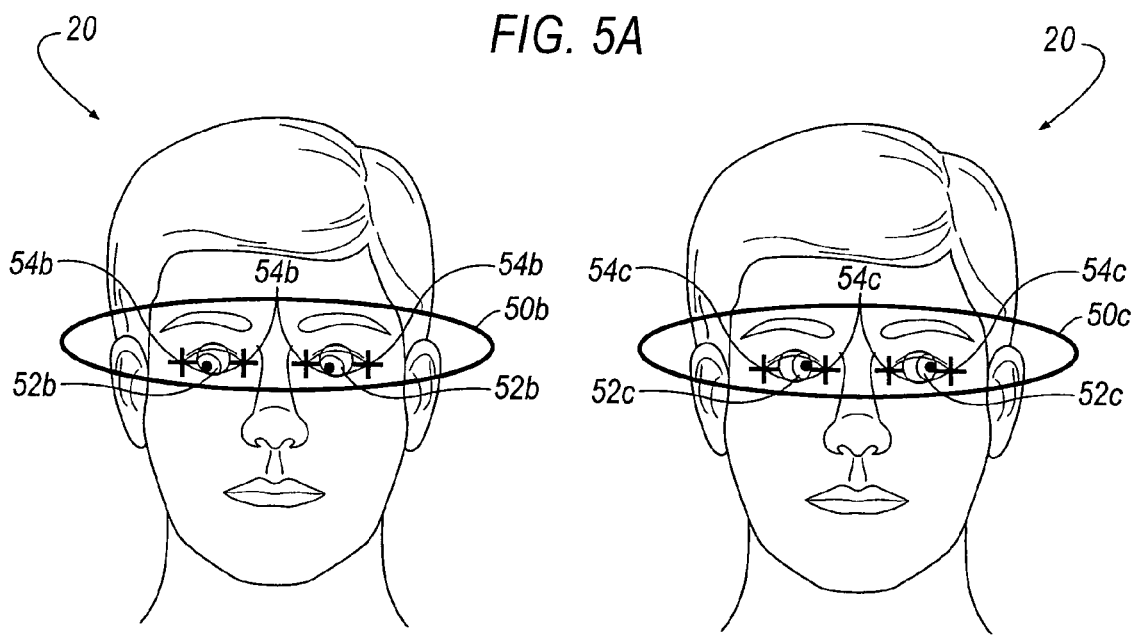
FIG. 5B
FIG. 5C

METHOD OF MITIGATING DRIVER DISTRACTION

RELATED APPLICATIONS

The present invention is a continuation-in-part of U.S. patent application Ser. No. 11/130,360 filed May 16, 2005 now abandoned, and assigned to the assignee of the present invention.

TECHNICAL FIELD

The present invention relates to driver distraction mitigation in motor vehicles, and more particularly to a method of determining when to initiate driver distraction mitigation.

BACKGROUND OF THE INVENTION

Each year numerous automobile accidents are caused by vehicle driver distractions. The National Highway Traffic Safety Administration (NHTSA) estimates that driver distraction is directly involved in twenty to thirty percent of all automobile accidents or roughly 1.6 million automobile accidents in the U.S. annually. Visual distraction of the driver is attributed to many of the accidents. For this reason, Delphi Automotive Inc. of Troy, Mich. has developed and demonstrated a real-time vision-based system that measures driver distraction based on eye gaze direction (on-road vs. off-road), and issues an alert if the proportion of off-road eye gaze over a specified period of time exceeds a threshold. See, for example, the proceedings of the 2006 International Consumer Electronics Show (CES) in Las Vegas, Nev., Jan. 4-8, 2006, and the aforementioned U.S. patent application Ser. No. 11/130,360.

Driver distraction alerts may take different forms and are primarily designed to provide visual, auditory or tactile feedback to stimulate re-orientation of the driver's attention to the forward road. When properly calibrated, this kind of system can beneficially train a driver to reduce the frequency and duration of off-road glances. However, it must be recognized that some off-road glances are normal and even desirable, and that driver alerts can themselves be a source of momentary distraction to an attentive driver. Accordingly, what is needed is a method of mitigating driver distraction that does not adversely affect the response time of an attentive driver.

SUMMARY OF THE INVENTION

The present invention is directed to an improved method of mitigating driver distraction in a motor vehicle, where driver alerts are issued based on both the proportion of off-road gaze time and the duration of a current off-road gaze. The driver alert is ordinarily issued when the proportion of off-road gaze exceeds a threshold, but is not issued if the driver's gaze has been off-road for at least a reference time. In vehicles equipped with forward-looking object detection, the driver alert is also not issued if the closing speed of an in-path object exceeds a calibrated closing rate.

BRIEF DESCRIPTION OF THE DRAWINGS

FIGS. 5A-5C illustrate views of a driver's ocular profiles;

DESCRIPTION OF THE PREFERRED EMBODIMENT

Figure 1:
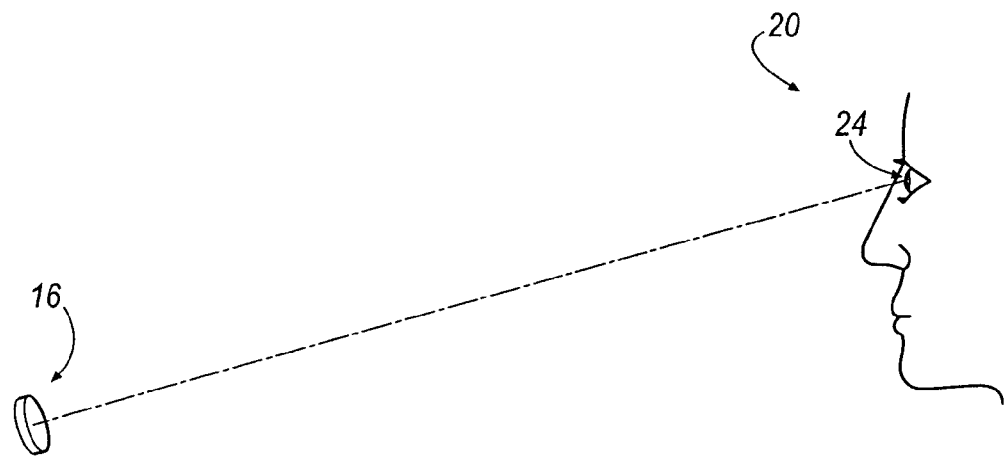
FIG. 1 is a general view of a driver attentiveness imaging system.
Figure 2:
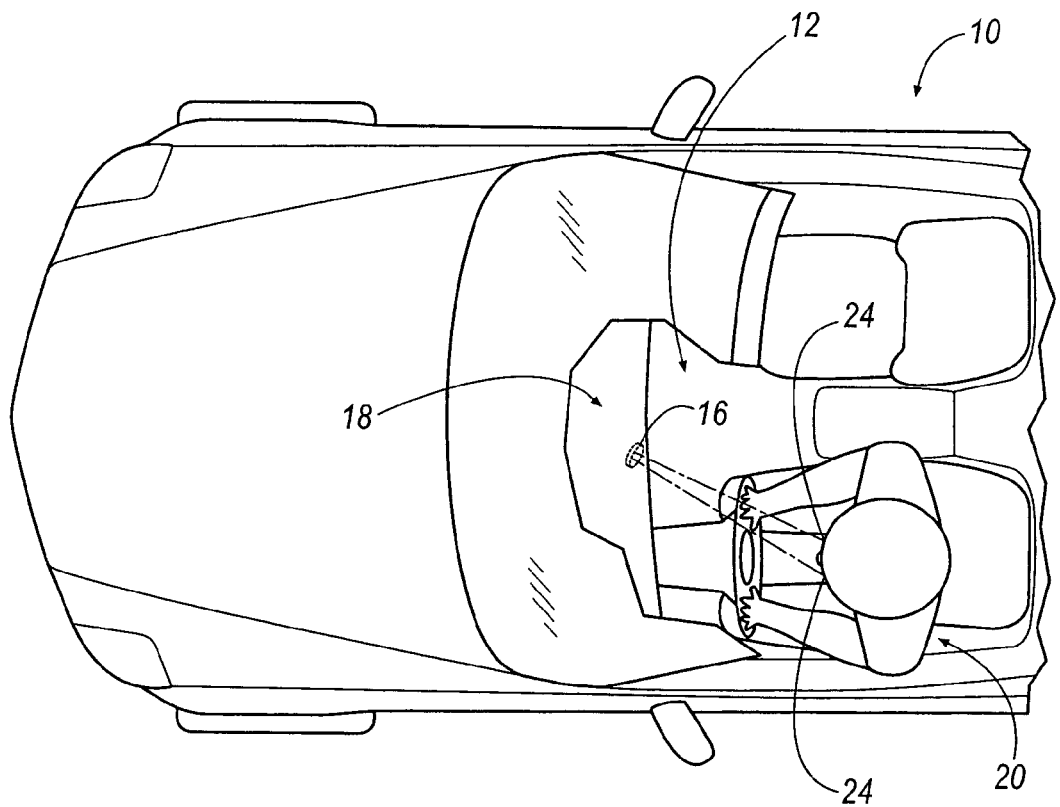
FIG. 2 is an environmental view of the driver attentiveness imaging system of FIG. 1.
Figure 3:
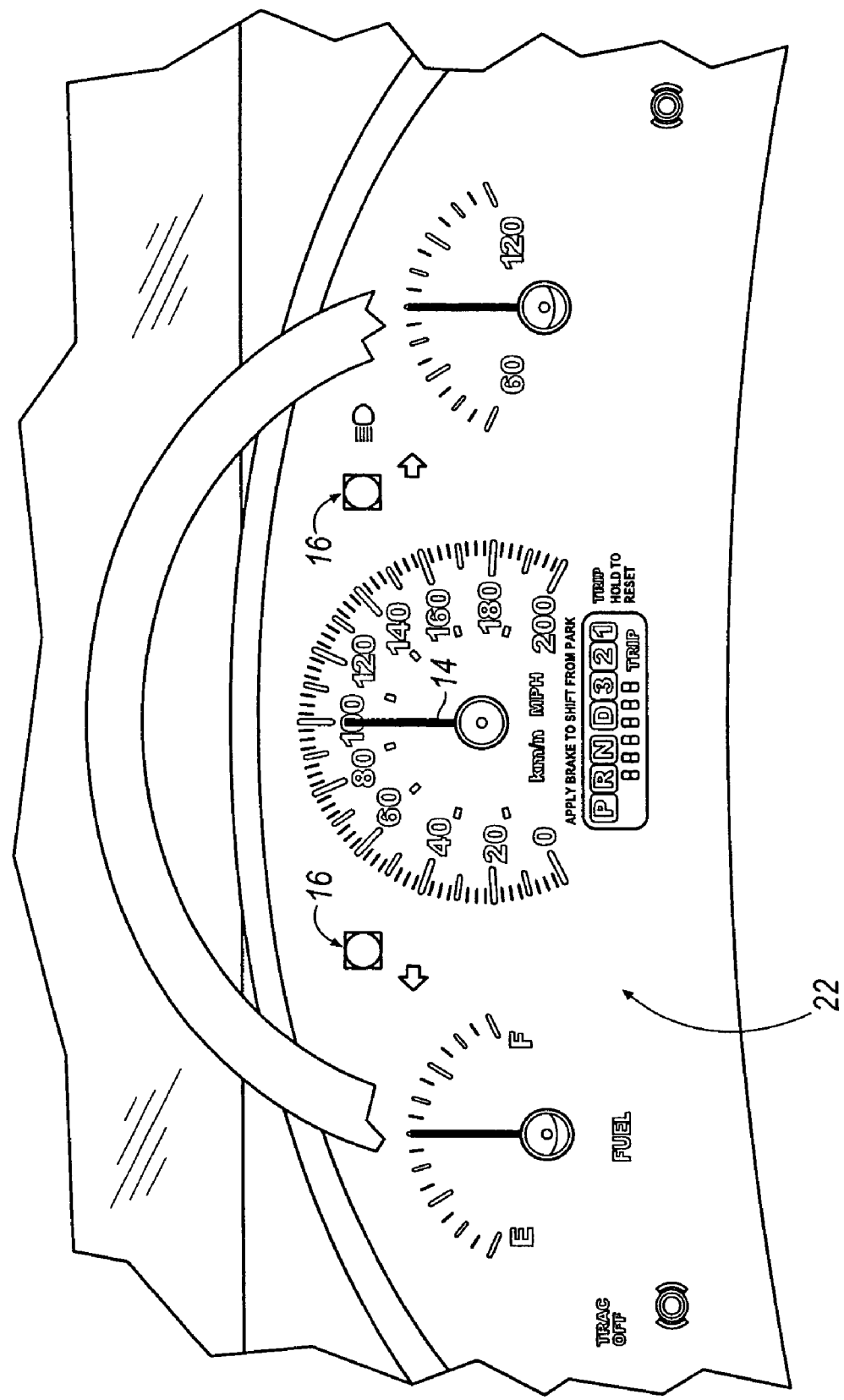
FIG. 3 is a view of an instrument panel including the driver attentiveness imaging device of FIG. 1.
Figure 4:
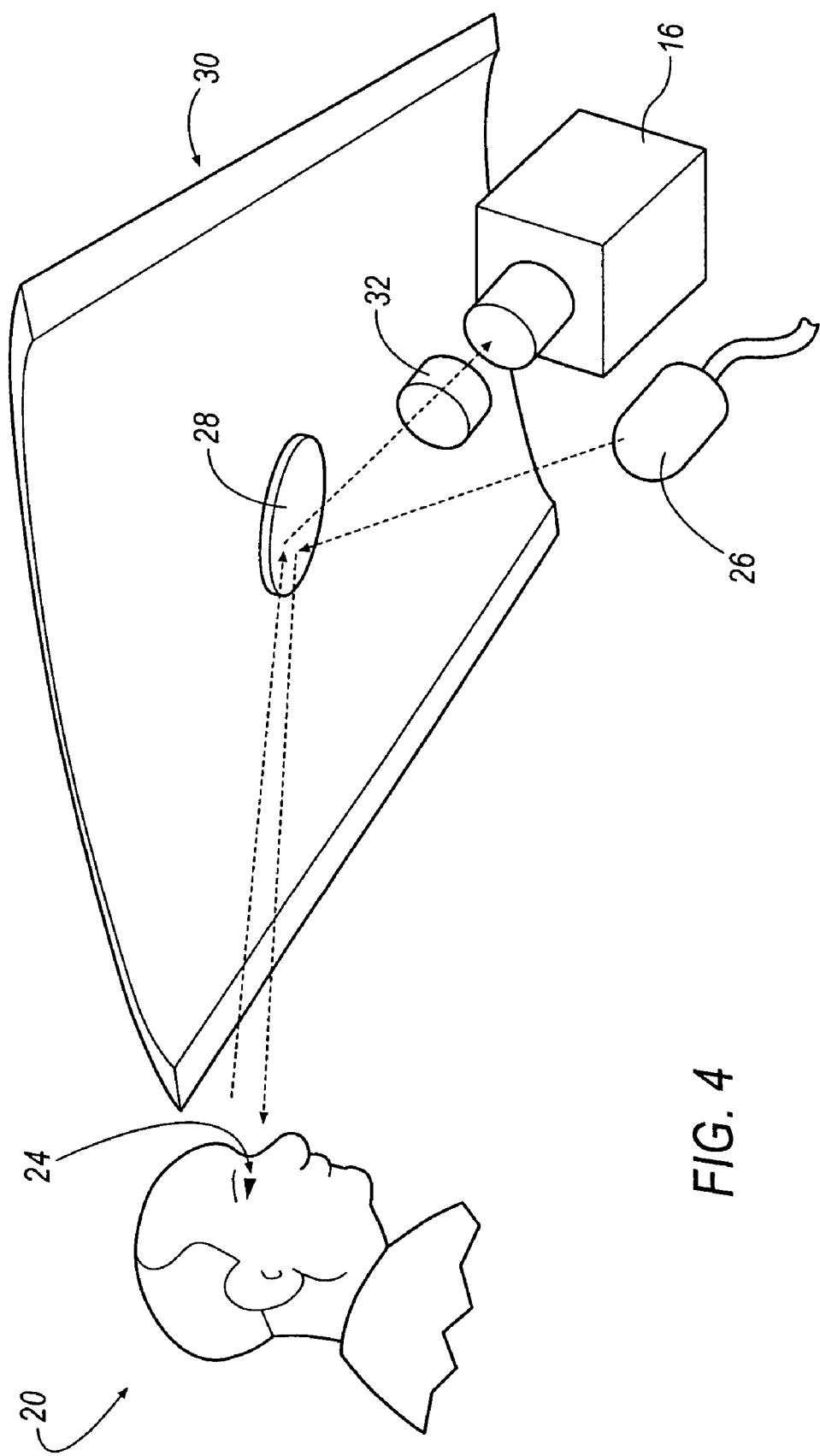
FIG. 4 is an environmental view of the driver attentiveness imaging system of FIG. 1.

Referring to FIGS. 1-2, the reference numeral 10 generally designates a host vehicle including a passenger compartment 12 and a video imaging camera 16. The camera 16 is part of a driver attentiveness imaging system, and may be positioned in a suitable location (such as on or within the instrument panel 18) for capturing images of eyes 24 of a driver 20. In the embodiment of FIG. 2, the camera 16 is mounted on a mid-region of the dashboard 18 in the front region of the passenger compartment 12. In the embodiment of FIG. 3, a pair of video imaging cameras 16 are mounted within an instrument panel cluster 22. In the embodiment of FIG. 4, reflected images of the driver's eyes 24 may be captured with an optical system including a video imaging camera 16, an illuminator 26, a mirror 28 located about an inboard surface of a windshield 30, and, if desired, a band-pass filter 32 to block ambient light that would otherwise saturate camera 16.

The camera 16 may include CCD/CMOS active-pixel digital image sensors mounted as individual chips onto a circuit board (not shown). One example of a CMOS active-pixel digital image sensor is Model No. PB-0330, commercially available from Photobit, which has a resolution of 640 H×480V. The use of digital image sensors for the video imaging camera 16 also allows for the detection of stereo information. The camera 16 may also be coupled to an eye tracking processor (not shown). The eye tracking processor may include a frame grabber for receiving the video frames generated by the camera 16. The camera 16 may also be coupled to a video processor for processing the video frames. The video processor includes memory, such as random access memory (RAM), read-only memory (ROM), and other memory as should be readily apparent to those skilled in the art. Other features of the driver attentiveness systems of FIGS. 1-4 are described in U.S. patent application Ser. Nos. 10/103,202; 10/291,913; 10/986,240; and 11/082,608, which have been assigned to the assignee of the present invention. Also see the U.S. Patent Application Publication Nos. US2003/0201895A1 and US2004/0090334A1, incorporated herein by reference.

Figure 6:
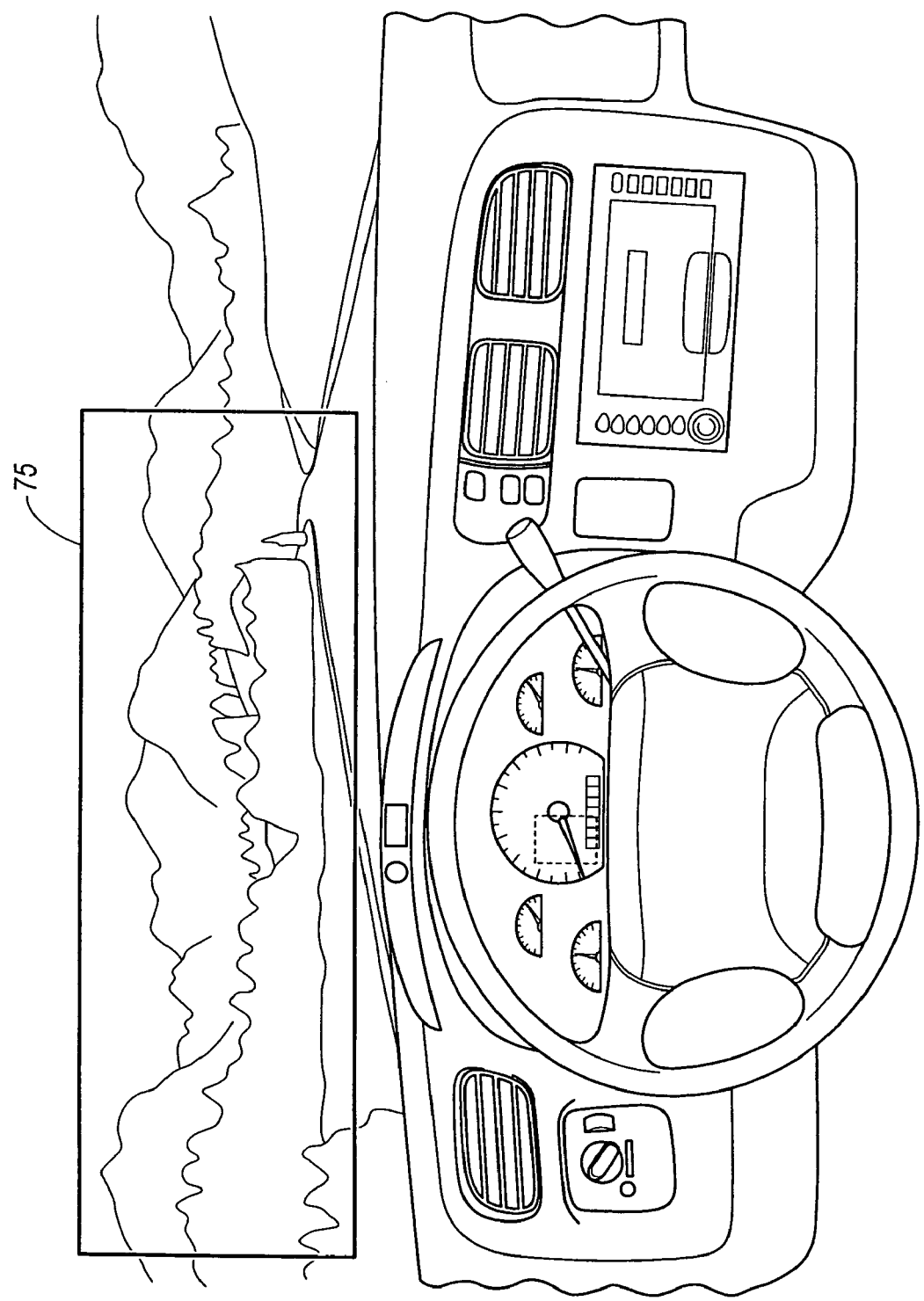
FIG. 6 illustrates a forward view window correlated to the ocular profile of FIG. 5A.

Referring to FIGS. 5A-5C, the driver attentiveness imaging systems described in FIGS. 1-4 captures ocular profiles. Examples of ocular profiles are shown generally at 50a, 50b, 50c in FIGS. 5A-5C, respectively, to identify the gazing patterns and attentiveness of the driver 20. The ocular profiles 50a, 50b, 50c include the position and size of the eyes 24, which is referenced generally at 52a, 52b, 52c and the corners of the eyes 24, which is referenced generally at 54a, 54b, 54c. In the following description, the ocular profile 50a is associated with an attentive driver 20 because the driver's eyes 24 are fixed on a 'forward view' of the road, which is generally correlated to a forward view window at reference numeral 75 in FIG. 6. Using the forward view window 75 as a reference for driver attentiveness, the ocular profiles 50b, 50c, for example, are associated with a non-attentive driver 20 who has a 'non-forward' or distracted view that is generally outside of the forward view window 75. For purposes of this invention, an ocular profile associated with a view outside the forward view window 75 is characterized as "off-road".

The driver attentiveness imaging system utilizes the ocular profile characterizations to determine if a driver alert should be issued to enhance the operation of host vehicle 10. The real-time duration and frequency of the driver's off-road ocular profile is evaluated to determine if the driver 20 is excessively distracted. This can occur, for example, when a particular task is being conducted by the driver 20, such as radio-tuning or cell-phone dialing, that distracts the driver 20 from maintaining attentiveness of the road ahead in the forward view window 75.

Figure 7:
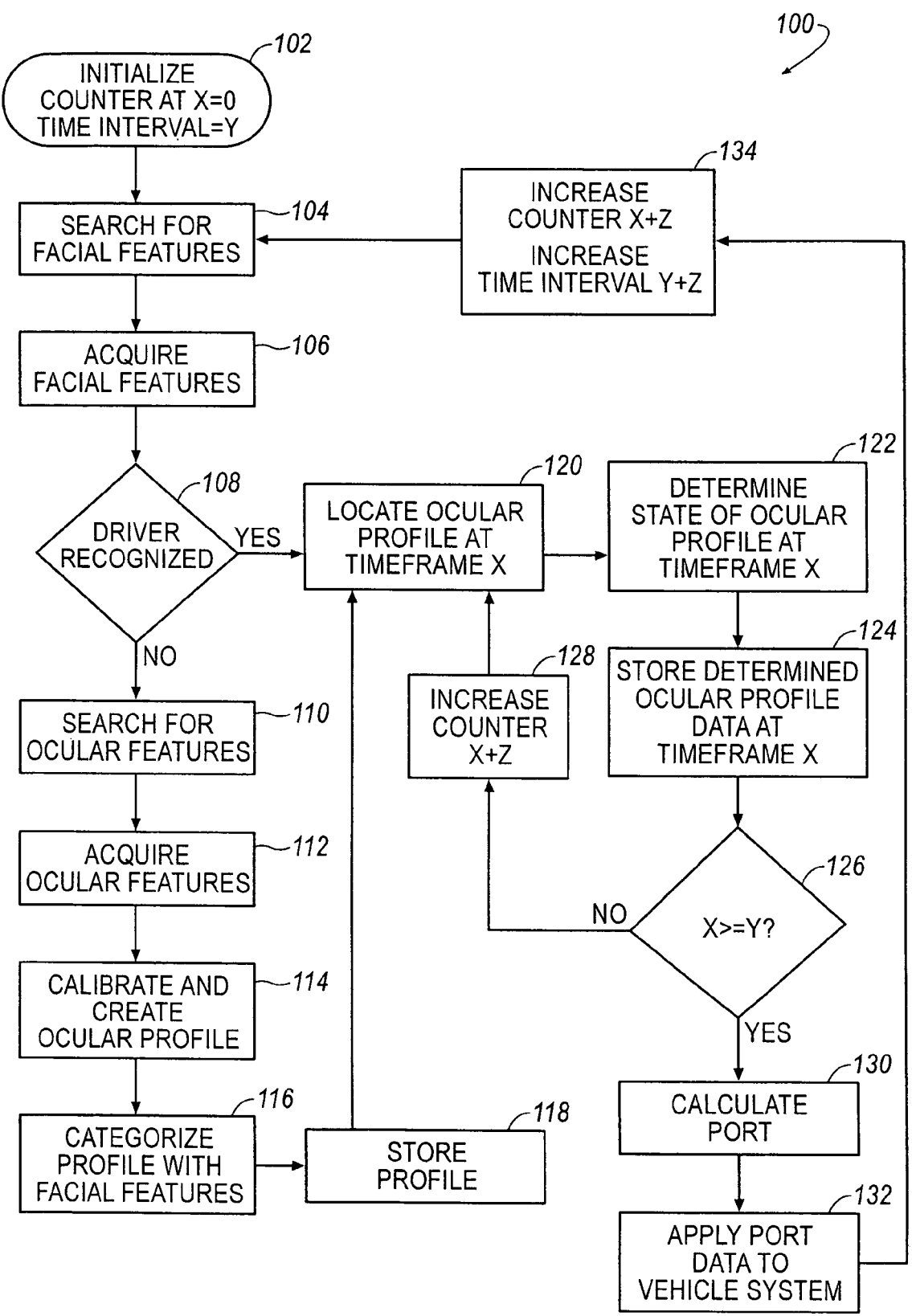
FIG. 7 is a flow diagram illustrating an algorithm carried out by the driver attentiveness imaging system of FIG. 1.

Referring to FIG. 7, a real-time, data-driven method for determining the visual distraction of the driver 20 is shown generally at 100. As generally seen in steps 102-134, a series of ocular profiles 50a, 50b, 50c is captured for subsequent analysis and application to a vehicle system responsible for issuing driver alerts for distraction mitigation. Steps 104-118 utilize the driver attentiveness imaging system to aquire facial and occular features of a driver 20. First, facial features are searched in step 104, and then, in step 106, the routine acquires the facial features. In a decision step 108, the routine determines if the driver 20 has been recognized. If the driver 20 has been recognized, the routine proceeds to step 120 to locate an ocular profile of the recognized driver 20. If the driver 20 has not been recognized from the facial features, the routine will search for and create a new ocular profile in steps 110 through 118. This includes searching for ocular features in step 110, acquiring ocular features in step 112, and calibrating and creating an ocular profile in step 114. In step 116, the ocular profile is categorized with facial features. Thereafter, the ocular profile is stored in memory in step 118 and the routine is advanced to step 120.

Referring now to steps 120, 122 and 124, a general examination of the ocular profiles 50a, 50b, 50c is conducted by locating, determining, and storing an imaged frame of the driver's ocular features at 52a-54c to characterize the state (i.e., on-road vs. off-road) of the captured ocular profile 50a, 50b, 50c. Steps 126 and 128 cycle the general examination of steps 120-124 within a time interval Y to capture sequentially imaged frames of the ocular profile 50a, 50b, 50c to determine a proportional amount of time that a driver's ocular profile is characterized as attentive (i.e., on-road) or distracted (i.e., off-road). Because the examined ocular profiles 50a, 50b, 50c are captured sequentially at step 124 on a frame-rate basis, real-time data can be calculated at step 130 to form a measure of the driver's visual distraction.

The real-time data calculated at step 130 is a percentage of a series of saved data from step 124. According to an embodiment, the calculated percentage may relate to distracted ocular profiles 50b, 50c captured over a given time interval Y. The calculation at step 130 is determined by summing frames of distracted ocular profiles 50b, 50c over the time interval Y and dividing the summed frames of distracted ocular profiles 50b, 50c over the time interval Y by a total series of frames captured over the time interval Y that includes attentive and distracted ocular profiles 50a, 50b, 50c. The expression for determining the calculation at step 130 is:

$$PORT = n/N$$

where "PORT" stands for Proportion of Off-Road glance Time, "n" is the number of frames that the driver's ocular profile is classified as a distracted ocular profile 50b, 50c, and N is a total number of predetermined series of frames (i.e. both attentive ocular profiles 50a and distracted ocular profiles 50b, 50c) to be captured over the time interval Y.

To calculate PORT, a counter value X is initialized at zero and the time interval Y is set to any desirable value in step 102. The values of X and Y are compared at step 126. Once the counter value X is greater than or equal to the value of the time interval Y that is associated with the total number of frames N, PORT is calculated at step 130. If X<Y, the algorithm is advanced to step 128 where the counter value X is incremented by an incrementation value Z. This loop at steps 120-128 is continuously cycled until the criteria at step 126 is met. The value of the counter X, time interval Y, and incrementation value Z, may be for example, 0.10 seconds, 0.25 seconds, 0.50 seconds, 1 second, 2 seconds, 3 seconds, 5 seconds, 10 seconds, 15 seconds, 30 seconds, or 60 seconds. Once a PORT value has been determined, block 132 outputs the PORT data to a vehicle system that determines if a driver alert should be issued for distraction mitigation.

Figure 8:
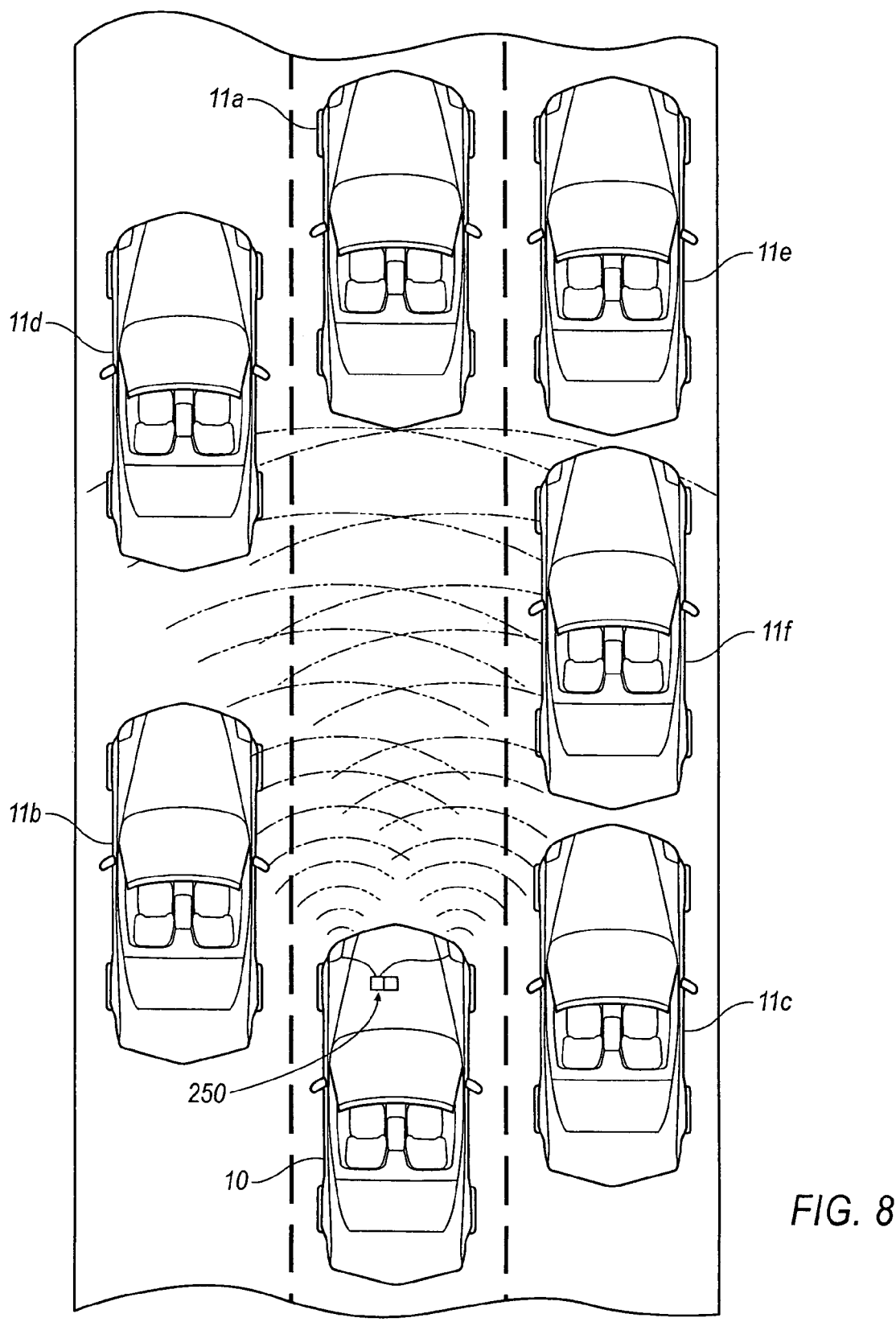
FIG. 8 is an environmental diagram of a host vehicle and other vehicles including an in-path vehicle.

According to the present invention, the vehicle system responsible for driver alerts evaluates the PORT data of FIG. 7 and in-path closing rate data of the host vehicle 10, if available, to determine if the driver alert should be issued. The in-path closing speed data is obtained from a forward-looking radar or laser sensor 250 such as depicted in the diagram of FIG. 8. The sensor 250 may be part of an automatic cruise control system or a crash avoidance system, for example. In any event, the sensor 250 scans a field-of-view forward of the host vehicle 10, identifies objects such as the vehicles 11a, 11b, 11c, 11d, 11e, 11f, and determines range and closing speed (i.e., range-rate) parameters in respect to an in-path vehicle 11a. The driver alert is ordinarily issued when the calculated PORT value exceeds a threshold, but is not issued according to this invention if the driver's gaze has been off-road for at least a reference time. If the host vehicle 10 is equipped with a forward-looking sensor 250, the driver alert is also not issued if the closing rate of an in-path object such as vehicle 11a exceeds a calibrated closing rate.

Figure 9:
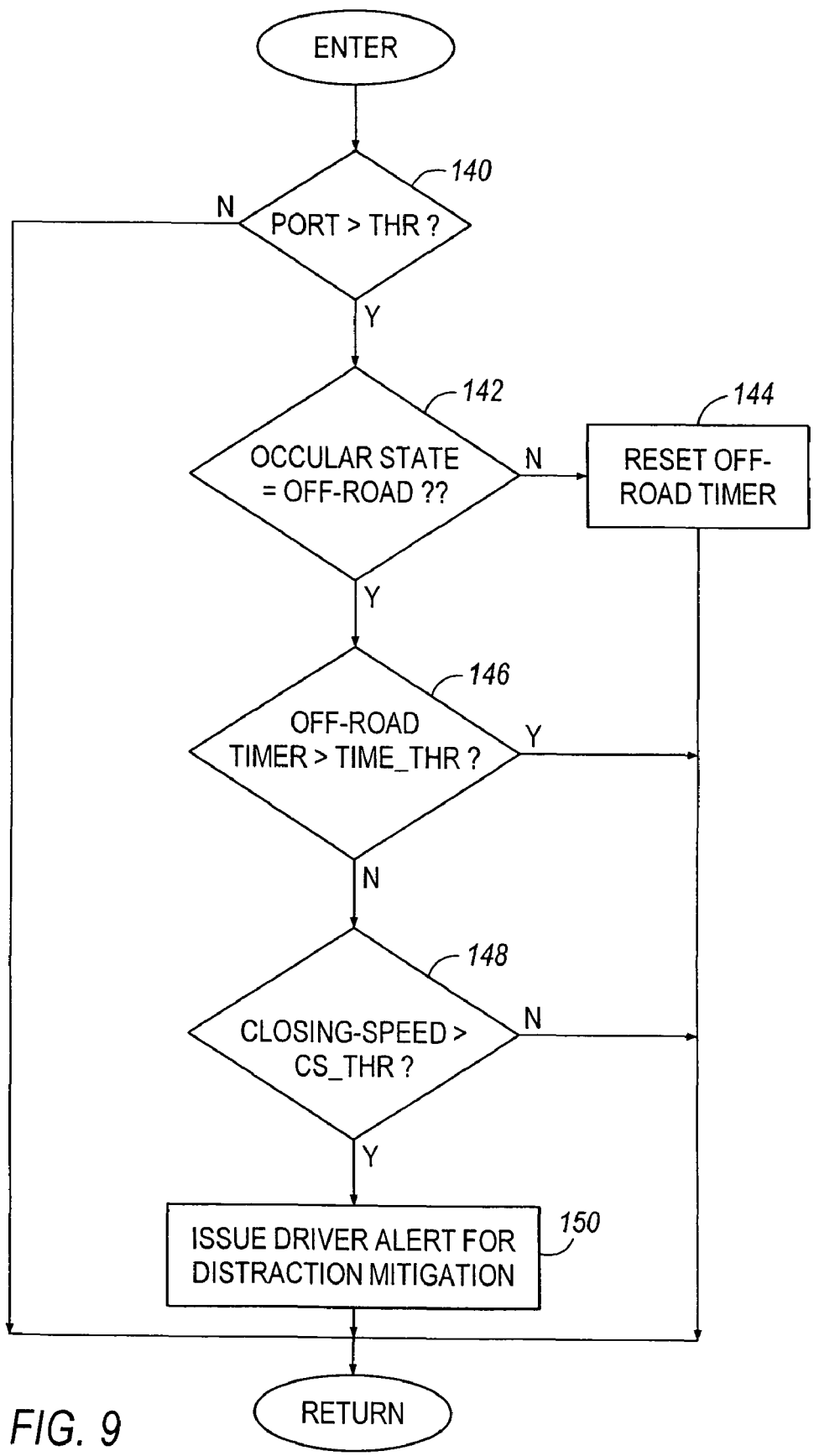
FIG. 9 is a flow diagram detailing a portion of the flow diagram of FIG. 7 pertaining to driver alert issuance.

The method outlined above is detailed in the flow diagram of FIG. 9, which represents a routine executed by the vehicle system responsible for issuing driver alerts for distraction mitigation. Referring to FIG. 9, the block 140 first compares the PORT value from FIG. 7 to a threshold THR to determine if there is an excessive level of driver distraction. If PORT≦THR, the driver distraction is not excessive, and no driver alert is issued. However, if PORT>THR, the blocks 142-150 are executed to determine if a driver alert should be issued. The block 142 determines if the current ocular state determined at block 122 of FIG. 7 is off-road. If not, the driver is looking at the forward road; no driver alert is issued, and block 144 resets an off-road timer used to measure the duration of a current distraction interval. If the current ocular state is off-road, block 146 compares the off-road timer to a time threshold TIME_THR. The setting of the threshold TIME_THR is based human factors research and represents the longest interval that a normal driver will ordinarily continuously glance off-road; in the illustrated embodiment, TIME_THR is calibrated to two seconds. Initially, the off-road timer will be less than TIME_THR, and block 148 is executed to determine if the forward-looking sensor 250 has detected an in-path vehicle 11a (or other object) having a closing rate that exceeds a threshold value CR_THR. By way of example, CR_THR may have a value such as −2 m/s, where the negative polarity of CR_THR indicates that the range between the host vehicle 10 and an in-path object such as the vehicle 11a in FIG. 8 is decreasing. This can occur when the host vehicle 10 approaches a stopped or slower-moving vehicle 11a, or when the in-path vehicle 11a decelerates. Alternately, the closing rate can be used to compute the deceleration of the in-path vehicle 11a, and the computed deceleration can be compared to a reference deceleration. In any event, block 150 is executed to issue a driver alert for distraction mitigation only if block 150 is answered in the negative.

In summary, the method of the present invention considers ocular state and in-path closing rate data (when available) to evaluate the desirability of issuing a driver alert for distraction mitigation in situations where the proportion of off-road gaze is considered to be excessive. If the driver's gaze is off-road, but has been off-road for less than TIME_THR (two second, for example), the driver alert is issued unless the sensor 250 detects an in-path vehicle 11a (or other object) and a closing rate that exceeds a threshold value CR_THR. Not issuing a driver alert under this condition allows the driver 20 to focus his or her full attention on the impending danger without being distracted by the driver alert. As a practical matter, vehicles having a forward looking sensor 250 are usually equipped with a collision warning system, and that system will issue an alert if the in-path vehicle 11a is deemed to pose a collision threat. If the host vehicle 10 is not equipped with a forward looking sensor 250, the block 150 will issue the driver alert if the driver's gaze is off-road, but has been off-road for less than TIME_THR. If the driver's gaze has continuously been off-road for longer than TIME_THR, the system assumes the driver 20 is about to glance back at the forward road, and a driver alert is not issued in order to avoid additional driver distraction.

While the present invention has been described with respect to the illustrated embodiment, it is recognized that numerous modifications and variations in addition to those mentioned herein will occur to those skilled in the art. Accordingly, it is intended that the invention not be limited to the disclosed embodiment, but that it have the full scope permitted by the language of the following claims.

The invention claimed is:

1. A method of mitigating distraction of a driver of a vehicle, comprising the steps of:

imaging an ocular profile of the driver and characterizing the ocular profile as off-road when detected ocular features of the ocular profile indicate that the driver's eyes are open and are not directed toward a forward view of the vehicle;
 determining a measure of driver distraction based on the ocular profile characterization;
 timing a current distraction interval that indicates a duration that the ocular profile is continuously characterized as off-road; and
 issuing a driver alert to mitigate driver distraction if the measure of driver distraction exceeds a threshold and the current distraction interval is less than a reference time.

2. The method of claim 1, including the step of:
 resetting the timed current distraction interval to zero when the ocular profile is not characterized as off-road.

3. The method of claim 1, where the measure of driver distraction is determined according to a proportion of a specified interval for which the ocular profile is characterized as off-road.

4. The method of claim 1, including the steps of:
 determining a closing speed between the vehicle and an in-path object if the measure of driver distraction exceeds said threshold and the current distraction interval is less than said reference time; and
 issuing said driver alert to mitigate driver distraction if the determined closing speed is greater than a reference speed.

5. The method of claim 1, including the step of:
 determining a deceleration of an in-path object if the measure of driver distraction exceeds said threshold and the current distraction interval is less than a reference time; and
 issuing said driver alert to mitigate driver distraction if the determined deceleration is greater than said reference deceleration.

6. The method of claim 1, where said reference time is approximately two seconds.

\* \* \* \* \*